(12) United States Patent
Drobkov et al.

(10) Patent No.: US 9,329,115 B2
(45) Date of Patent: May 3, 2016

(54) FLUID DENSITY MEASUREMENT DEVICE

(75) Inventors: Vladimir Drobkov, Moscow (RU);
Vladimir Melnikov, N. Novgorod (RU);
Andrey Shustov, Nijmegen (NL)

(73) Assignee: NEST INTERNATIONAL N.V., Curacao (AN)

( * ) Notice: Subject to any disclaimer, the term of this patent is extended or adjusted under 35 U.S.C. 154(b) by 853 days.

(21) Appl. No.: 13/265,021

(22) PCT Filed: Apr. 22, 2010

(86) PCT No.: PCT/NL2010/000071
§ 371 (c)(1),
(2), (4) Date: Dec. 1, 2011

(87) PCT Pub. No.: WO2010/126358
PCT Pub. Date: Nov. 4, 2010

(65) Prior Publication Data
US 2012/0150452 A1    Jun. 14, 2012

(30) Foreign Application Priority Data
Apr. 29, 2009    (EP) .................................... 09159014

(51) Int. Cl.
*G01R 25/00* (2006.01)
*G01N 9/00* (2006.01)

(52) U.S. Cl.
CPC ...................... *G01N 9/002* (2013.01)

(58) Field of Classification Search
CPC ..................................................... G01N 9/002
USPC ......................................... 702/25; 73/861.19
See application file for complete search history.

(56) References Cited

U.S. PATENT DOCUMENTS

| 4,177,669 A | 12/1979 | Wenger |
| 4,524,610 A | 6/1985 | Fitzgerald et al. |

(Continued)

FOREIGN PATENT DOCUMENTS

| JP | S6177985 S | 12/1987 |
| JP | 2006-52996 A | 2/2006 |

(Continued)

OTHER PUBLICATIONS

EP Search Report for priority EP application (EP09159014.1) of PCT/NL2010/000071.
International Search Report for PCT/NL2010/000071.
Japanese Office Action dated Dec. 11, 2013; Patent Application No. 2012-508414.
Office Action in related Tawainese application 099112941 dated Jun. 6, 2014 and English Translation.
Office Action in related Israeli Patent Application No. 215624, mailed Aug. 4, 2015.

*Primary Examiner* — Gregory J Toatley
*Assistant Examiner* — Stephanie Bloss
(74) *Attorney, Agent, or Firm* — Troutman Sanders LLP; Ryan A. Schneider

(57) ABSTRACT

A device for determining a density of a fluid including a mechanical resonator, a driver/receiver unit arranged to provide an actuation to the mechanical resonator, sense a response of the mechanical resonator to the actuation, and provide an output signal representing the response; and an evaluation unit. The evaluation unit of the device is arranged to determine an oscillation distribution from the output signal, determine a resonance frequency estimate from the oscillation distribution, and determine the density of the fluid based upon the resonance frequency estimate. The device enables a more accurate determination of the fluid density for fluids including immiscible components (thus forming a heterogeneous mixture), like a water-oil emulsion, or a fluid with occluded gas.

16 Claims, 2 Drawing Sheets

(56) References Cited

U.S. PATENT DOCUMENTS

| | | |
|---|---|---|
| 4,796,468 A | 1/1989 | Blake-Coleman et al. |
| 4,831,885 A | 5/1989 | Dahlin |
| 5,533,381 A | 7/1996 | Seale |
| 6,845,663 B2 * | 1/2005 | Lopatin et al. ............... 73/290 V |
| 2006/0131994 A1 | 6/2006 | D'Angelico et al. |
| 2007/0027638 A1 * | 2/2007 | Fernald et al. ................. 702/25 |
| 2007/0203601 A1 | 8/2007 | Izumi et al. |
| 2009/0120168 A1 * | 5/2009 | Harrison ................ G01N 9/002 73/54.24 |
| 2009/0126506 A1 * | 5/2009 | Heimel et al. ............. 73/861.19 |

FOREIGN PATENT DOCUMENTS

| | | |
|---|---|---|
| JP | 2006052996 A | 2/2006 |
| RU | 2349897 C2 | 3/2009 |
| WO | 9524630 A1 | 9/1995 |

* cited by examiner

FLUID DENSITY MEASUREMENT DEVICE

FIELD OF TECHNOLOGY

The present invention relates to a device for measuring the density of a fluid in different, including aggressive, media both at normal conditions and in high-pressure environment. As an example, it may be applied in crude oil and gas production and transportation systems, in chemical and petrochemical production, as well as in fuel and energy industries, etc.

BACKGROUND ART

Devices for measuring or determining the density of a fluid are known per se. The operating principle of such known devices is e.g. based on applying a low-frequency mechanical resonator submersed in a fluid of which the density is to be determined. In this respect, reference can e.g. be made to Patent of the Russian Federation No. 2 291 403, U.S. Pat. No. 4,922,745, U.S. Pat. No. 6,389,891, U.S. Pat. No. 6,845,663. Due to the influence of the added mass of a medium (e.g. a fluid), the resonance frequency of the mechanical resonator changes. Known devices e.g. comprise a measurement circuit for determining an occurring resonance frequency shift which may then be used to calculate a required density value. Known mechanical resonators e.g. include a tuning fork which, due to its symmetric design, prevent the transfer of oscillations to the body of the sensor and, therefore, excludes the influence of the surrounding metal parts on the frequency characteristics of the resonator. To determine the resonance frequency, various electronic circuits can be used, e.g. scanners of the amplitude-frequency response of a resonator or positive-feedback systems self-triggering at a resonance frequency.

Despite satisfactory performance, the known device may have one or more of the following disadvantages.

Firstly, if used to measure the density of a fluid consisting of immiscible components (heterogeneous mixture), like a water-oil emulsion, the properties of a medium surrounding the tuning fork may cause a variation of the resonance characteristic and thus an uncertainty in the resonance frequency measurement, thereby adversely affecting the measurement accuracy.

Secondly, the known device has been found to be unsuited to measure the density of a fluid containing occluded gas, since the presence of such occluded gas may cause considerable and abrupt changes in the resonance frequency thus influencing its mean value and compromising the determination of the fluid density.

In view of the above, it is an object of the present invention to provide a device for determining a density of a fluid with an increased accuracy, in particular for fluids comprising immiscible components (thus forming an heterogeneous mixture), like a water-oil emulsion; or a fluid with occluded gas.

SUMMARY OF THE INVENTION

According to an aspect of the invention, there is provided a device for determining a density of a fluid, the device comprising
 a mechanical resonator,
 a driver/receiver unit arranged to provide an actuation to the mechanical resonator, sense a response of the mechanical resonator to the actuation, and provide an output signal representing the response; and
 an evaluation unit for determining a resonance frequency of the mechanical resonator based on the output signal of the driver/receiver unit,
 characterized in that
 the evaluation unit being arranged to
  determine an oscillation distribution from the output signal and
  determine a resonance frequency estimate from the oscillation distribution.
  determine the density of the fluid based upon the resonance frequency estimate.

The device according to the invention enables the density of a fluid to be determined based on the determination of a resonance frequency estimate obtained from an oscillation distribution.

In order to determine the density of a fluid, the device according to the invention comprises a mechanical resonator which, during use, is at least partly immersed in the fluid of which the density is to be determined. Examples of suitable mechanical resonators are rods, tuning forks, T-shaped resonators, etc. . . . . In an embodiment, the mechanical resonator is a tuning fork having a basis mounted to the driver/receiver unit of the device.

The driver/receiver unit as applied in the device according to the invention is arranged to, in use, perform the following:
 provide an actuation to the mechanical resonator,
 sense a response of the mechanical resonator to the actuation,
 provide an output signal representing the response.

In order to realize this, the driver/receiver unit can e.g. comprise an actuator (e.g. an electromagnetic or piezo-electric actuator) for actuating the mechanical resonator.

The driver/receiver unit as applied in the device according to the invention is further equipped to sense a response of the mechanical resonator to the actuator. In response to an actuator, the mechanical resonator will undergo a displacement and will oscillate or vibrate. Such an oscillation or vibration of the mechanical resonator can be sensed by the driver/receiver unit, e.g. by a vibration sensor. The vibration or oscillation can e.g. be determined by a velocity sensor or an acceleration sensor (e.g. accelerometer) or a displacement sensor. As will be acknowledged by the skilled person, various implementations are feasible for sensing an oscillation or vibration of the resonator. In an embodiment, the driver/receiver unit comprises a piezo-electric element arranged to both provide the actuation (when operating in an actuating mode, i.e. as an actuator) and the sensing (when operating in a sensing mode, i.e. as a sensor).

The driver/receiver unit is further arranged to provide an output signal representative of the response of the mechanical resonator to the actuation. As an example, the output signal can be an electric signal proportional to e.g. a displacement or velocity or acceleration of the mechanical resonator, the signal e.g. being provided by a sensor of the driver/receiver unit.

The device according to the invention further comprises an evaluation unit for determining a resonance frequency estimate of the mechanical resonator. In accordance with the invention, the resonance frequency estimate is determined by the evaluation unit from an oscillation distribution that is determined from the output signal of the driver/receiver unit. It is submitted that, in case of the application of the mechanical resonator in a fluid comprising immiscible components (thus forming an heterogeneous mixture) like e.g. a water-oil emulsion, or a fluid with occluded gas the resonator may oscillate or vibrate at different frequencies at different instances. Monitoring the vibrational behavior of the mechanical resonator over a period of time may thus result in an oscillation distribution rather than a single, specific oscillation at a specific (resonance) frequency. From such an oscillation distribution, the evaluation unit as applied in the device according to the invention, can determine an estimate for the resonance frequency of the fluid.

In accordance with the invention, an oscillation distribution is determined from the output signal of the driver/receiver unit. Within the meaning of the present invention, an oscillation distribution can e.g. include, but is not limited to, a distribution of the oscillation periods as observed in the output signal. Equally, within the meaning of the present invention, a frequency spectrum (e.g. obtained by applying a Fourier transformation to the output signal) of the output signal, i.e. a spectrum representing the frequency content of the vibration or oscillation of the mechanical resonator, can be considered an oscillation distribution. As will be acknowledged by the skilled person, an oscillation can be characterized by a period (or duration) of the oscillation or by a frequency of the oscillation (the frequency being the inverse of the period). As such, an oscillation distribution can equally be represented by a frequency distribution or an oscillation period distribution. As will be described in more detail below, the oscillation distribution can be obtained in different ways. As an example, using an counter and a comparator, the output signal as obtained from the driver/receiver unit can be monitored by the evaluation unit during a certain period (either predetermined or continuously) whereby the duration of each period (or a number representative of the duration) is memorized, e.g. in a memory unit of the evaluation unit.

From the oscillation distribution, the evaluation unit can further determine a resonance frequency estimate (e.g. from a peak value or a median value or a mean value of the oscillation distribution) and determine a density value for the fluid surrounding the mechanical resonator (e.g. based on a difference between the measured/determined resonance frequency estimate and a nominal resonance frequency, i.e. the resonance frequency of the mechanical resonator when not immersed).

In an embodiment, the evaluation unit can comprise a computational unit (e.g. comprising a microcontroller, a microprocessor or the like) for determining the resonance frequency estimate from the oscillation distribution and determining the density of the fluid based upon the resonance frequency estimate.

In an embodiment, the evaluation unit comprises a measurement unit for obtaining the oscillation distribution. The measurement unit can e.g. comprise a comparator arranged to receive and compare the output signal to a predetermined value (e.g. zero), a counter, a write register (in general, a memory unit) of the counter state and a high-frequency oscillator. In an embodiment, an output of the comparator can be connected to the write register of the counter state. By counting a number of pulses (e.g. provided by the high-frequency oscillator) occurring during a period of the output signal, an oscillation period value is obtained which can be stored in a memory unit. By repeating this process during a comparatively large period of time, an oscillation distribution can be obtained representing a distribution of the oscillation periods that occurred in response to the actuation.

The measurement unit and computational unit may be designed with a microprocessor. Such a microprocessor can be further applied, in an embodiment of the invention, to determine a resonance frequency estimate, e.g. as a mean value of the oscillation period of the mechanical resonator. Alternatively, or in addition, the microprocessor can evaluate at least two values of the oscillation period of the mechanical resonator using a polyfunctional probability density distribution curve. Such a curve, e.g. a polynomial, can be used to, e.g. by curve-fitting, to evaluate the oscillation distribution and e.g. determine one or more peak values of the oscillation period The device according to the invention may further comprise a sensor to measure a characteristics of the mechanical resonator or fluid, e.g. a temperature of the resonator or fluid or a pressure of the fluid.

The device according to the invention may further comprise a display for displaying the oscillation distribution and/or the fluid density that is determined.

These and other aspects of the invention will be more readily appreciated as the same becomes better understood by reference to the following detailed description and considered in connection with the accompanying drawings in which like reference symbols designate like parts.

DESCRIPTION

Figure 1:
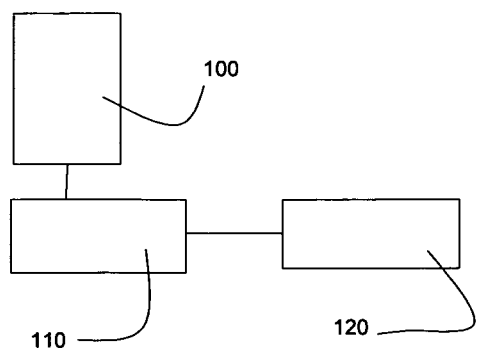
FIG. 1 schematically depicts an embodiment of a device according to the invention.

The present invention relates to a device for measuring a density of a fluid. Known devices for determining the density of a fluid e.g. comprise a sensor arranged to sense an oscillation of a mechanical resonator, e.g. actuated by an actuator (whereby sensor and actuator can be combined in a driver/receiver unit), and an evaluation unit for determining the density of a measured medium (e.g. a fluid) by determining a change of the resonance frequency of the mechanical resonator. The device according to the invention, of which an embodiment is schematically depicted in FIG. 1, differs from known devices in that it comprises an evaluation unit arranged to determine an oscillation distribution. By analyzing the oscillation distribution of the mechanical resonator, it is possible to obtain statistically valid information about a density fluctuation of the measured medium (e.g. a fluid) surrounding the mechanical resonator. As a result, an improved accuracy for the measurements of the density of fluids can be realized. In particular, it has been notices that the device according to the invention can provide an improved accuracy in determining a fluid density for fluids comprising immiscible components (thus forming a heterogeneous mixture) like a water-oil emulsion or a fluid with occluded gas. As shown in FIG. 1, the device according to the invention comprises a mechanical resonator 100 and a driver/receiver unit 110 for applying an actuation to the resonator, sensing a response of the resonator to the actuation and providing an output signal representative of the response. As an example, the driver/receiver unit can comprise one or more piezoelectric elements for actuating the resonator and/or sensing the resonator's response. The resonator can e.g. be actuated by a pulsed signal, e.g. provided by a high frequency oscillator. The signal for actuating the mechanical resonator may also comprise a noise signal (i.e. a signal comprising a plurality of different frequency components) thereby exciting the mechanical resonator at different frequencies. As shown in FIG. 1, the device according to the invention further comprises an evaluation unit 120, the evaluation unit being arranged to:

determine an oscillation distribution from the output signal, determine a resonance frequency estimate from the oscillation distribution, and determine the density of the fluid based upon the resonance frequency estimate.

In an embodiment, the evaluation unit is arranged to determine an oscillation distribution from the output signal by sampling the output signal as received by the driver/receiver unit. In practice, the mechanical resonator can be designed such that its operating resonance frequency ranges between 1 000 and 10 000 Hz (thus having an oscillation period between 0.1-1.0 ms). In case a tuning fork is used as a resonator, this can be achieved mainly by changing the cross-section and the length of the tuning fork prongs. Choosing this frequency range is e.g. based on the following considerations. The oscillating frequency should be as low as possible to increase the effective thickness of the wall layer of a fluid, which reduces the influence of the heterogeneity of the measured fluid. This may however lead to an increased length of the tuning fork prongs, which makes them less stable in the flow, the whole structure becoming bulky and unusable in real-life environment when a tuning fork is placed in a pipe containing an oil-water-gas flow. This explains why usually tuning forks with a resonance frequency not less than 1 200 Hz are used. Based upon the expected frequency range of the mechanical resonator, a suitable sampling frequency can be determined for sampling the output signal. Preferably, the sampling frequency is equal or above the Nyquist-frequency of the expected response of the resonantor. When such a sampled output signal is obtained (the evaluation unit may e.g. comprise a dedicated measurement unit for such sampling), a frequency spectrum (in general, an oscillation distribution) can be obtained by applying a Fourier transformation (e.g. a discrete Fourier transformation) to the sampled output signal. From the frequency spectrum, the evaluation unit (or a computational unit of the evaluation unit) can determine a resonance frequency estimate e.g. as a peak value of the frequency spectrum. Based on the resonance frequency estimate, the evaluation unit can derive a value for the density of the fluid examined by comparing the resonance frequency estimate with a reference resonance frequency of the resonator, e.g. a resonance frequency of the resonator applied in air or a fluid with a known density. To take into account a temperature factor, a temperature sensor, e.g. a semiconductor or a platinum resistance thermometer, can further be provided to measure the temperature of the fluid surrounding the resonator and/or the mechanical resonator itself.

Figure 2:
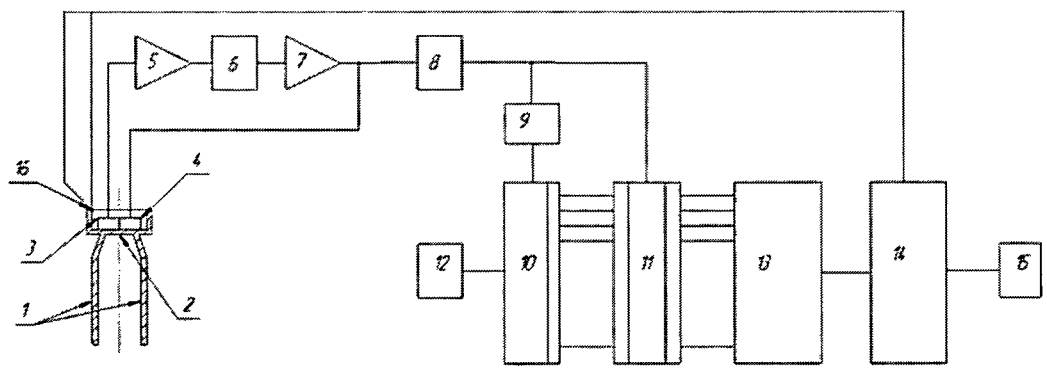
FIG. 2 schematically depicts another embodiment of a device according to the invention.

FIG. 2 schematically depicts another embodiment of the device according to the invention. The device comprises a mechanical resonator (e.g. a tuning fork 1) secured to a membrane 2, and a driver/receiver unit (e.g. a bimorph piezoelectric element) comprising receiving 3 and emitting 4 piezo-electric elements. Receiving 3 and emitting 4 piezoelectric elements are connected to an electronic circuit comprising a preamplifier 5, its input being connected to the receiving piezo-electric element 3, a phase-correction circuit 6, and a final amplifier 7, its output linked to the emitting piezo-electric element 4. In the example shown, the final amplifier 7 is further connected to a comparator 8 which forms output pulses. The comparator 8 is connected to a counter 10 through a counter reset pulse former 9 and to a write register of the counter state 11. The counter is linked to the output of a high-frequency oscillator 12. The output of the write register of the counter state 11 is connected to a measurement block 13 arranged to determine an oscillation distribution based on the output of the write register. The measurement block 13 is further linked to a computational unit 14 with a display unit 15. The mechanical resonator is further provided with a temperature sensor 16. Elements 5-14 of the embodiment as depicted in FIG. 2 can be considered an example on how to realize the evaluation unit as applied in the device according to the invention.

In the device as schematically depicted in FIG. 2, a density measurement of a fluid is performed by a (statistical) analysis of an oscillation distribution which can e.g. be derived by monitoring the oscillation period history. The mechanical resonator (the tuning fork) oscillates at a resonance frequency F due to the application of an actuation by the driver/receiver unit, e.g. by controlling the emitting piezo-element 4 by the electronic circuit (elements 5, 6, 7). In general, the frequency of the tuning fork resonator ranges within 1 200-5 000 Hz. As a result, an AC voltage (i.e. the output signal as can be applied to determine an oscillation distribution) with a period of $T=1/F$ is generated at the output of the amplifier 7. This period depends on the density of a medium where the resonator is immerged into. In accordance with the embodiment of the present invention, the oscillation or vibration of the resonator can be monitored during a certain number of periods whereby the length of the periods is determined (or a value indicative of the length is determined) for each period. In accordance with the embodiment as described in FIG. 2, the length of each period can be measured as described below. The high frequency oscillator 12 may continuously generate high-frequency pulses at a frequency of e.g. 16 MHz. Prior to each measurement the counter reset pulse former 9 resets the counter 10 to a zero-state e.g. upon detection of the start of a period (e.g. when a displacement of the resonator corresponds to a neutral position) or when the output signal (e.g. representative of the displacement or velocity or acceleration of the resonator) value is zero or a predetermined value. The counter 10 counts, during each period the number of input high-frequency pulses. Before the occurrence of a counter reset pulse, the data obtained from the counter is written to the write register 11 (in general, a memory unit), e.g. by an output pulse from the comparator 8. It results a binary number written in the write register 11, proportional to an oscillation period T. The register contents are recorded to the memory of the measurement block 13 and also to the computing unit 14. Then the process is repeated iteratively for a number of periods resulting in an oscillation distribution, in the embodiment as described, an oscillation period distribution.

When the data is being accumulated the microprocessor may generate a graph (e.g. on the display unit 15 of the embodiment as shown representing a distribution of the length of the periods as measured and due to changes in the fluid density over the time. The graph or graph data may further be applied (e.g. by the computational unit 14) to evaluate the density of the fluid (e.g. a heterogeneous medium, e.g. comprising immiscible components, like a water-oil emulsion, or occluded gas) by e.g. calculating a mean value of the period length. The computational unit 14 may e.g. apply one or more probability criteria for determining an average or mean period length. It is worth noting that the calculated value of the period length can be considered the inverse of the resonance frequency estimate as described above. Determining, using a probability criterion, a value representing the period length as observed in the measurements can thus be considered an example of determining a resonance frequency estimate from the oscillation distribution.

When the tuning fork (in general, the mechanical resonator) is immersed into a fluid and actuated, it oscillates at a frequency determined by the density of the medium. As a result, a signal having a corresponding frequency can be generated at the output of the comparator 8. The distance between two positive fronts of the signal may e.g. be equal to a length of the period. If a fluid is a homogenous medium, its density is constant and the oscillation period (and thus the length of the period) is stable. An oscillation distribution curve would thus narrow to a vertical line in such case. Its position on a time base (abscissa) wholly determines a required density of the fluid without any additional evaluation.

Figure 3A:
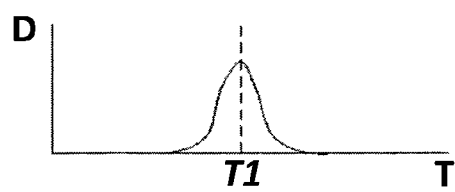
FIG. 3a schematically depicts an oscillation distribution of a first heterogeneous fluid.

In case the fluid is a heterogeneous medium, its density may vary, and the tuning fork may thus be located in a flow of a fluctuating density. As a consequence, the oscillation period (or length of the oscillation period) begins to vary within a certain range, which causes a spreading of the oscillation period distribution. A typical oscillation distribution for slightly heterogeneous fine-dispersed fluids, e.g. oil-water mixtures, is shown in FIG. 3a. FIG. 3a schematically depicts the occurrence or probability density (D) of the oscillation periods in the output signal as a function of the oscillation period length (T1). The maximum of the distribution curve (T) determines a mean fluid density in the first approximation. A further statistical analysis may further enhance the validity of the result, e.g. by analyzing probability deviation, trend analysis, or even the running order of the mechanical resonator can be evaluated.

Figure 3B:
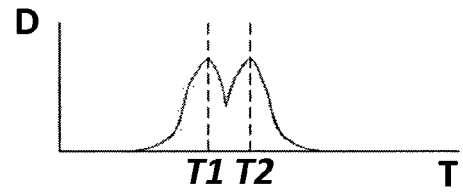
FIG. 3b schematically depicts an oscillation distribution of a second heterogeneous fluid.

A typical oscillation distribution for pronounced heterogeneous fluids, e.g. oil-gas mixture, is shown in FIG. 3b. The position of the distribution maxima (T1,T2) can be used to determine which of them represents a liquid phase, and which accounts for a gas. Having distinguished the part related to oil (the longer period) its density can be evaluated.

As an example of an implementation of a device according to the invention, the following can be mentioned:
tuning fork resonators, fork length 40 mm, equivalent diameter 4 mm,
bimorph drive with a piezoelectric element, diameter of the element 10 mm, thickness 0.2 mm;
tuning fork material—stainless steel;
operating frequency of the sensor—about 3 800 Hz.
standard microchips and a microprocessor have been used in the electrical circuit.
The device as described has been tested in different fluids, specifically, in water, mineral oil, solvents, chemical agents, liquefied gases whereby steady and reliable performance of the device has been observed in all of the test fluids.

As required, detailed embodiments of the present invention have been disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention. The mere fact that certain measures are recited in mutually different dependent claims does not indicate that a combination of these measures cannot be used to advantage.

The term coupled, as used herein, is defined as connected, although not necessarily directly, and not necessarily mechanically.

A single processor or other unit may fulfil the functions of several items recited in the claims.

The invention claimed is:

1. A device for determining a density of a heterogeneous fluid, the device comprising:
   a mechanical resonator, during use being at least partly immersed in a heterogeneous fluid of which the density is to be determined,
   a driver/receiver unit arranged to provide an actuation to the mechanical resonator, sense a response of the mechanical resonator to the actuation, and provide an output signal representing the response, and
   an evaluation unit for determining a resonance frequency estimate of the mechanical resonator based on the output signal of the driver/receiver unit,
   wherein the evaluation unit is arranged to:
      monitor the output signal during a period of time and obtain a plurality of oscillation period values wherein an oscillation period value is the number of pulses occurring during a period of the output signal,
      determine an oscillation distribution representing a distribution of the oscillation period values that occurred in response to the actuation with respect to time,
      determine a resonance frequency estimate from the oscillation distribution, and
      determine the density of the heterogeneous fluid based upon the resonance frequency estimate,
      and wherein the evaluation unit comprises a computational unit arranged to determine at least two resonance peak values from the oscillation distribution using a polyfunctional probability density distribution curve.

2. The device according to claim 1, wherein the computational unit is arranged to:
   determine the resonance frequency estimate from the oscillation distribution, and
   determine the density of the fluid based upon the resonance frequency estimate.

3. The device according to claim 2, wherein the evaluation unit comprises a measurement unit for determining an oscillation distribution from the output signal, and
   wherein the output signal represents a sampling of the response of the mechanical resonator.

4. The device according to claim 2, wherein the computational unit is arranged to apply a Fourier transformation for determining the resonance frequency estimate from the oscillation distribution.

5. The device according to claim 2, wherein the oscillation distribution comprises an oscillation period distribution derived from the output signal, and
   wherein the oscillation period distribution comprises an array of oscillation period values derived from the output signal by determining a duration of a plurality of subsequent oscillation periods of the output signal and storing a value representing the duration in the array.

6. The device according to claim 2, wherein the computational unit comprises a microprocessor for:
   determining the resonance frequency estimate from the oscillation distribution, and
   determining the density of the fluid based upon the resonance frequency estimate.

7. The device according to claim 2, wherein:
the computational unit is arranged to determine a mean value of the oscillation period of the mechanical resonator.

8. The device according to claim 1 further comprising a display for displaying the oscillation distribution.

9. The device according to claim 1, wherein:
an oscillation period of the mechanical resonator is within the range of 0.1-1.0 ms.

10. The device according to claim 1 further comprising:
a sensor for measuring a characteristic of one or both of the fluid and the mechanical resonator.

11. The device according to claim 10, wherein the sensor comprises a temperature sensor.

12. The device according to claim 10, wherein the sensor comprises a pressure sensor.

13. The device according to claim 1, wherein the driver/receiver unit comprises one of an electromagnetic actuator or a piezo-electric actuator for providing the actuation to the mechanical resonator.

14. The device according to claim 1, wherein the driver/receiver unit further comprises a piezo-electric sensor for sensing the response of the mechanical resonator to the actuation.

15. The device according to claim 1, wherein the mechanical resonator is selected from the group consisting of a tuning fork, a rod, and a T-shaped resonator having a basis mounted to the driver/receiver unit.

16. A device for determining a density of a heterogeneous fluid, the device comprising:
a mechanical resonator, during use being at least partly immersed in a heterogeneous fluid of which the density is to be determined,
a driver/receiver unit arranged to provide an actuation to the mechanical resonator, sense a response of the mechanical resonator to the actuation, and provide an output signal representing the response, and
an evaluation unit for determining a resonance frequency estimate of the mechanical resonator based on the output signal of the driver/receiver unit,
wherein the evaluation unit is arranged to:
monitor the output signal during a period of time and obtain a plurality of oscillation period values wherein an oscillation period value is the number of pulses occurring during a period of the output signal,
determine an oscillation distribution representing a distribution of the oscillation period values that occurred in response to the actuation with respect to time,
determine a resonance frequency estimate from the oscillation distribution, and
determine the density of the heterogeneous fluid based upon a difference between the determined resonance frequency estimate and the resonance frequency of the mechanical resonator when not immersed,
and wherein the evaluation unit comprises a computational unit arranged to determine at least two resonance peak values from the oscillation distribution using a polyfunctional probability density distribution curve.

* * * * *